United States Patent [19]

van der Knaap

[11] Plant 4,909

[45] Oct. 26, 1982

[54] CHRYSANTHEMUM NAMED CHERRY WESTLAND

[75] Inventor: Jacques C. M. van der Knaap, De Lier, Netherlands

[73] Assignee: Pan-American Plant Company, Parrish, Fla.

[21] Appl. No.: 193,090

[22] Filed: Oct. 2, 1980

[51] Int. Cl.[3] ..... A01H 5/00

[52] U.S. Cl. ..... Plt./79

[58] Field of Search ..... Plt./74–83

*Primary Examiner*—James R. Feyrer

*Attorney, Agent, or Firm*—Chas. W. Rummler

[57] ABSTRACT

A new and distinct chrysanthemum cultivar, for greenhouse culture to produce cut flowers, distinguished by a unique bronze coloration. This new variety is a radiation developed sport of the variety "Westland" and in substantially all respects, except coloration, the new plant is like its parent. The title of this application is the European denomination for this variety. In the United States, this variety is marketed as "Westland Brandy".

5 Drawing Figures

BACKGROUND OF THE NEW PLANT

This new chrysanthemum plant originated as a sport of "Westland" (U.S. Plant Pat. No. 4,589) produced by me by radiation of the parent in 1976 at De Lier, Holland, with the object of developing new varieties for the commercial market. The unique bronze coloration of this plant led me to produce it by means of cuttings at De Lier, Holland, and continued propagation through successive generations has shown that the novelty of the original plant holds true from generation to generation and appears to be firmly fixed. This plant is now being propagated for commercial purposes at West Chicago, Ill.; Cortez, Fla.; and De Lier, Holland.

DESCRIPTION OF THE DRAWINGS

This chrysanthemum cultivar is illustrated by the accompanying drawings, of which sheet 1 is a full color photographic rendition of a group of the flowers of the new plant taken when in full bloom, sheet 2 shows a full color view of a flower of this plant showing its actual coloration as bloomed in January in Florida and an enlarged picture of the same flower showing the petal formation and arrangement, and sheets 3 and 4 are mechanical prints of photocopies of the front and back sides, respectively, of typical leaves of the new variety.

DESCRIPTION OF THE NEW PLANT

The following is a detailed description of my new variety of chrysanthemum based upon observations made at West Chicago, Ill., U.S.A., in the summer of 1980 and in Florida in January 1982, with color designations according to the R.H.S. Colour Chart published by The Royal Horticultural Society of London, England.

THE PLANT

Origin: Sport developed by radiation breeding.
Parentage: Westland (U.S. Plant Pat. No. 4,589).
Classification:
- *Botanic.*—*Chrysanthemum morifolium.*
- *Commercial.*—Greenhouse plant for cut flowers.

Form: Perennial herbaceous bush with cymose inflorescence.
Height: About 100 to 125 cm.
Growth: Terminal; strong, strict and vigorous.

Growth rate: Rapid.
Branching: None.
Foliage:
- *Quantity.*—Abundant.
- *Leaf size.*—Length — about 40 to 120 mm. Width — about 20 to 70 mm.
- *Shape.*—Ovate with cleft margin.
- *Venation.*—Pinnate.
- *Texture.*—Leathery.
- *Color.*—Upper side — 147A. Under side — 147B.
- *Petioles.*—Length: About 20 to 30 mm.

THE BUD

Form: Globular.
Size: Bud varies in both diameter and depth.
Opening rate: Normal.
Color of florets:
- *When phyllaries first divide.*—161C.
- *When petals begin to unfurl.*—161C.

Phyllaries:
- *Number.*—Approximately 15.
- *Shape.*—Lanceolate.
- *Color.*—138A.

Peduncle:
- *Character.*—Rigid and erect.
- *Length.*—Various.
- *Surface texture.*—Canescent.
- *Color.*—138D.

THE FLOWER

Blooming habit: Normally intermittent.
Recommended flowering: Year around with photoperiod control.
Blooms:
- *Flower type.*—Composite and quilled.
- *Size.*—Medium. Diameter — about 70 to 80 mm. Depth — about 10 to 15 mm.
- *Borne.*—Cymose.
- *Shape.*—When bloom first opens — cup-shaped. When bloom matures — flat.

Florets:
- *Number.*—Many ray florets; few disc florets.
- *Arrangement.*—Imbricated.
- *Form.*—Quill, open tipped with entire margin and rounded and incised apex.
- *Texture.*—Soft.

*Appearance.*—Satiny.

*Color.*—Outer florets: Upper side — 179C-D but tipped with 179B. Inner florets: Upper side — 179A-B. The flower colors of this variety vary according to the season of flowering, as well as environmental conditions, and range from 182C to 179A-B.

Flower stem:

*Length.*—Varies.

*Character.*—Strong and upright.

*Color.*—138D.

Persistence: Florets hang on and dry.

Fragrance: Typical chrysanthemum.

Lasting quality:

*On plant.*—4 weeks.

*As cut flower.*—4 weeks.

REPRODUCTIVE ORGANS

Stamens: Few in syngenesious arrangement.

*Anthers.*—Size: Insignificant. Color: Yellow.

*Filaments.*—Insignificant.

*Pollen.*—Color: None.

Pistils:

*Number.*—One to each ray floret.

*Styles.*—Color: Greenish-Yellow.

*Stigma.*—Color: Greenish-Yellow.

Ovaries: Inferior bicarpellate.

This new variety of chrysanthemum plant is distinguished mainly by the unique bronze color of its flowers. Otherwise this new plant is essentially the same as its parent in all practical respects.

I claim:

1. A new and distinct chrysanthemum cultivar, substantially as herein shown and described, characterized particularly by the unique bronze coloration of its flowers.

* * * * *

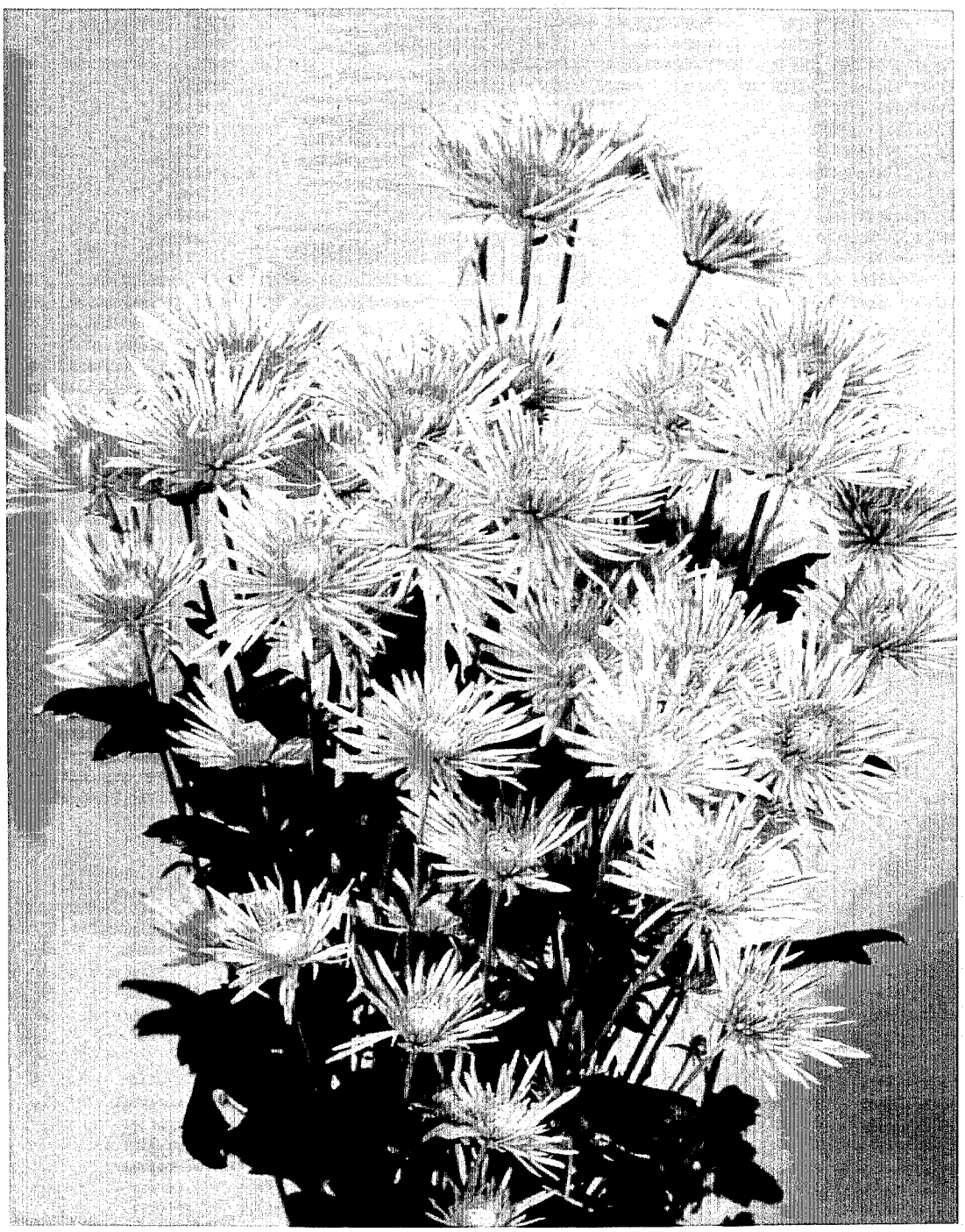

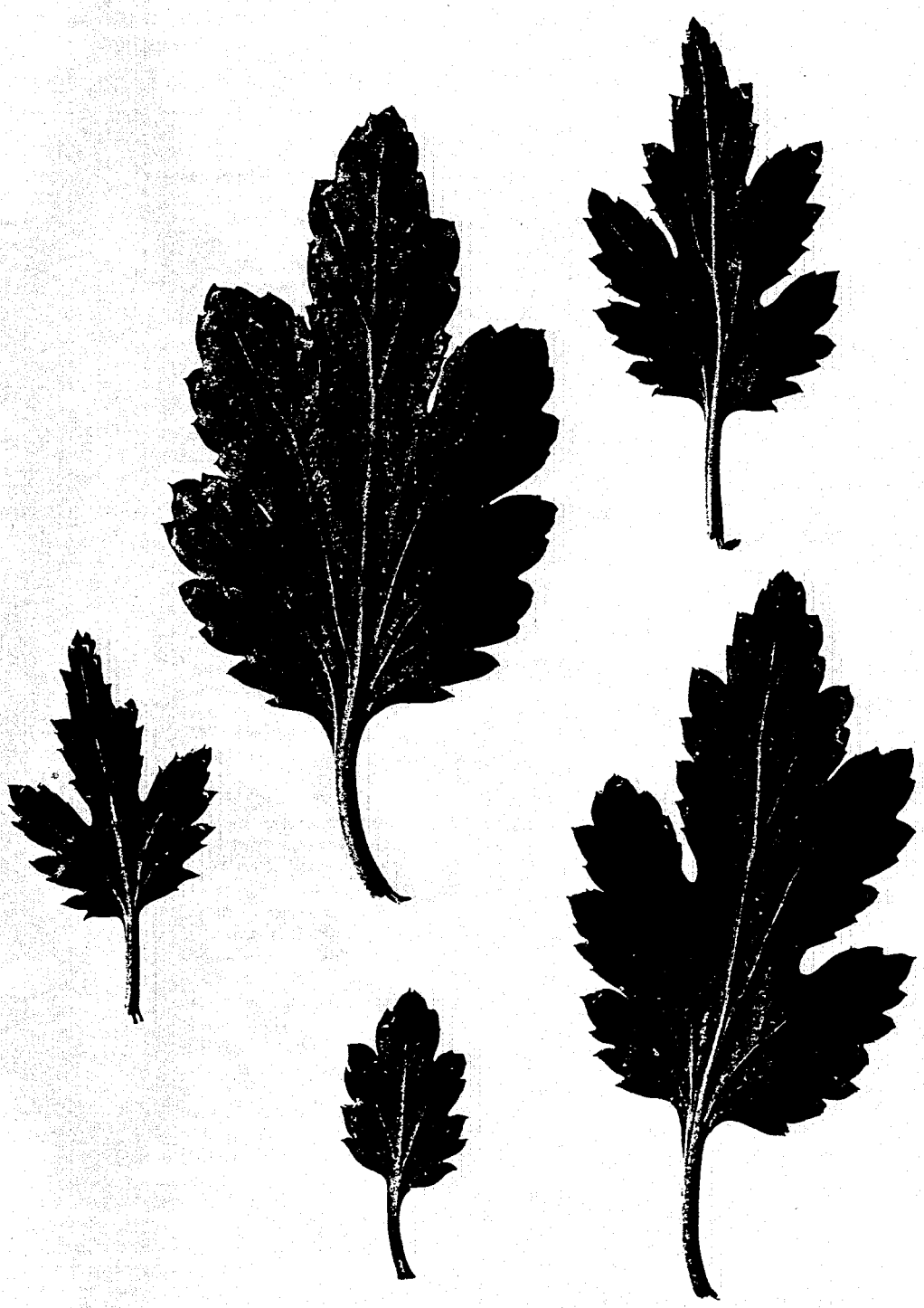

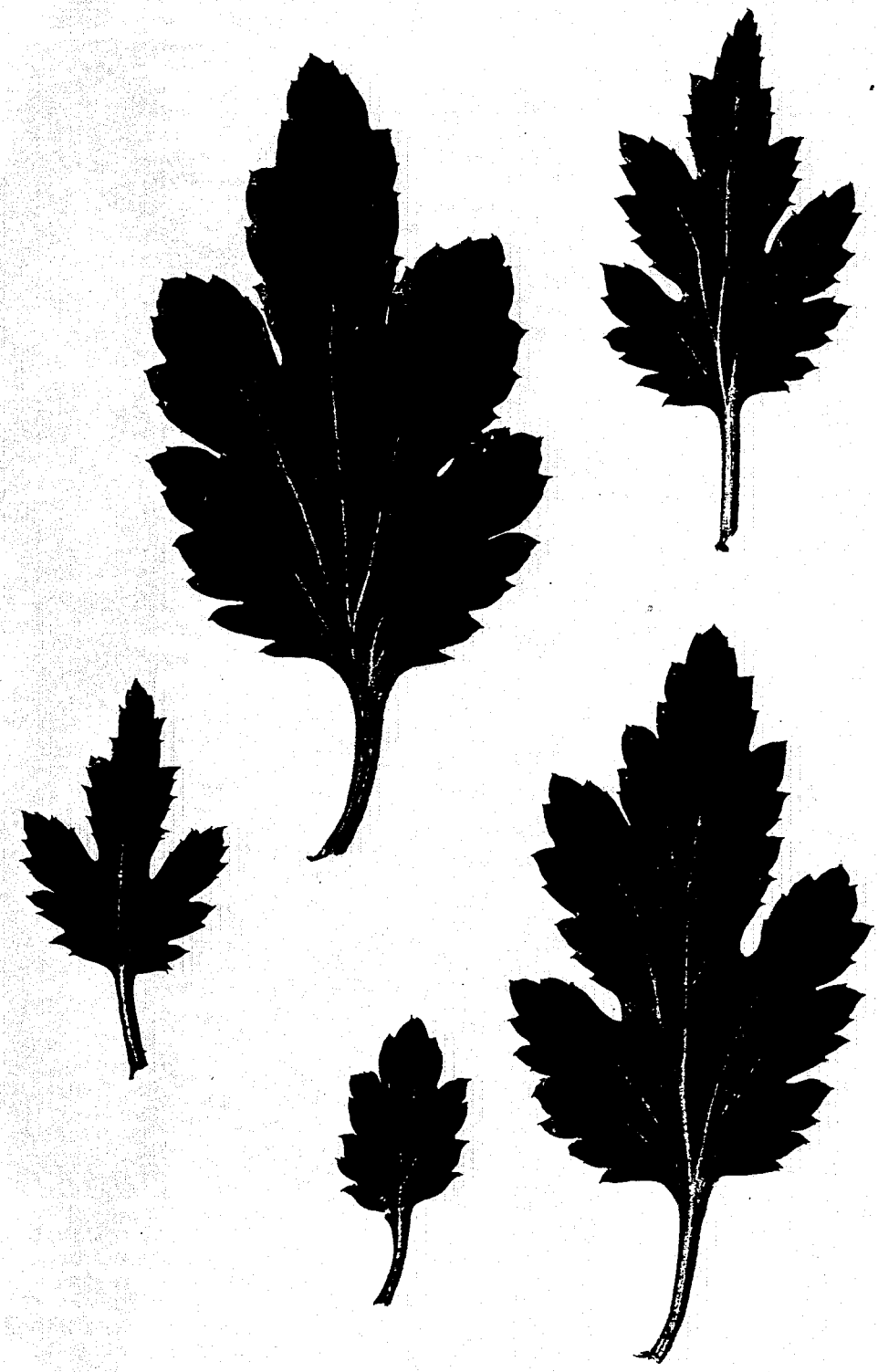

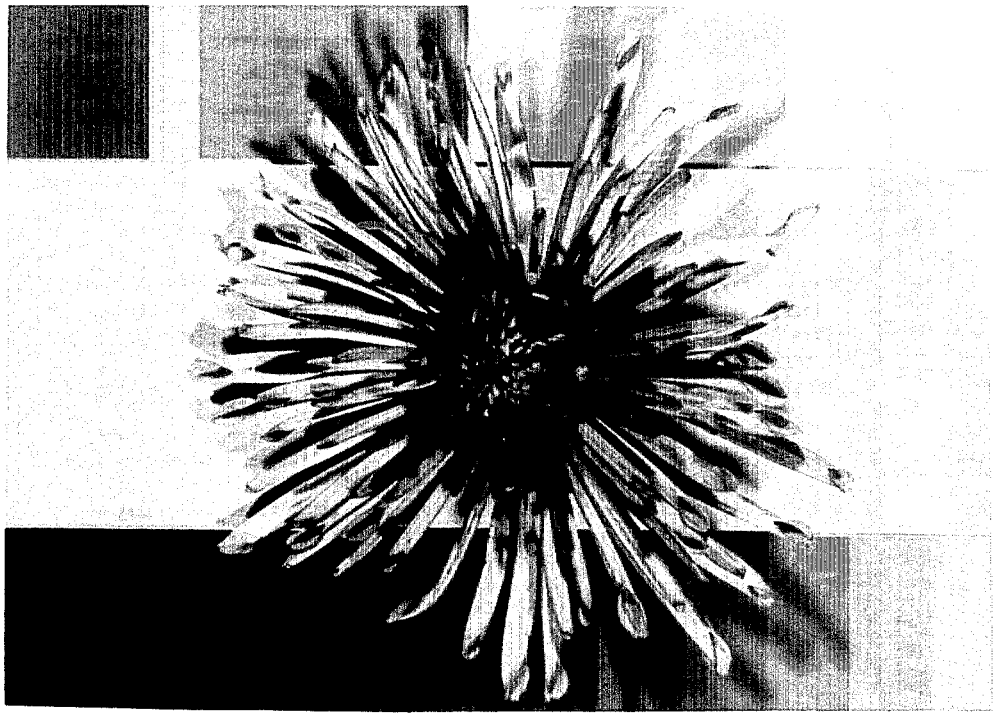
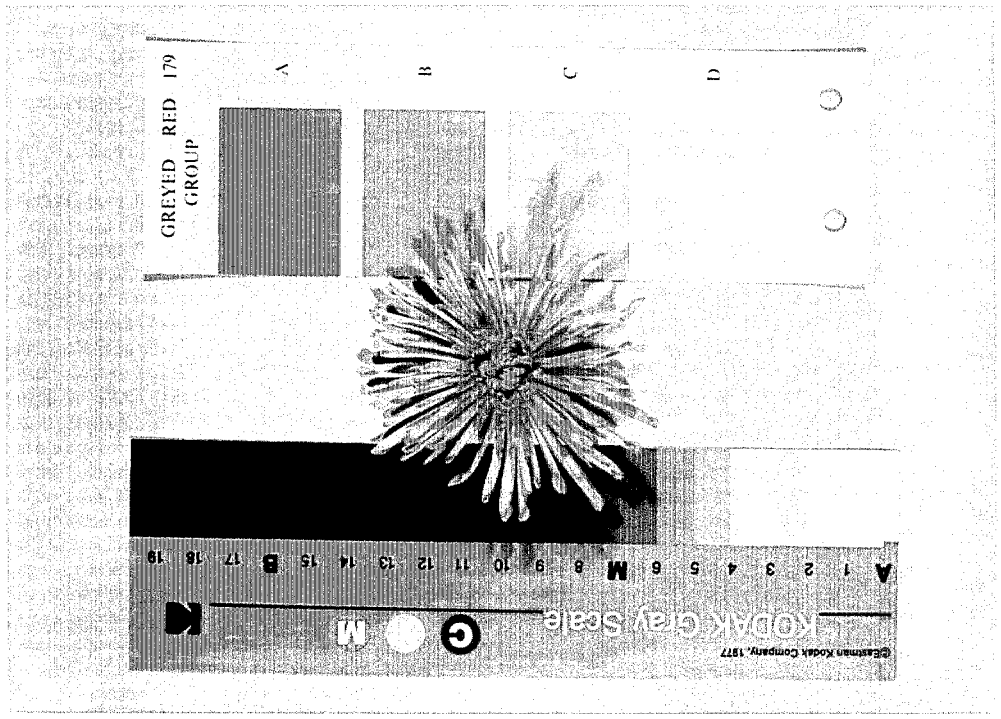
©Eastman Kodak Company, 1977
KODAK Gray Scale
A 1 2 3 4 5 6 M 8 9 10 11 12 13 14 15 B 17 18 19
GREYED RED 179
GROUP
A
B
C
D